United States Patent [19]

LaMattina et al.

[11] 4,452,987

[45] Jun. 5, 1984

[54] HALOACETYL IMIDAZOLES

[75] Inventors: John L. LaMattina, Ledyard; Christopher A. Lipinski, Waterford, both of Conn.

[73] Assignee: Pfizer Inc., New York, N.Y.

[21] Appl. No.: 449,129

[22] Filed: Dec. 13, 1982

Related U.S. Application Data

[60] Division of Ser. No. 293,574, Aug. 20, 1981, Pat. No. 4,374,843, which is a continuation-in-part of Ser. No. 196,231, Oct. 14, 1980, abandoned.

[51] Int. Cl.³ .......................................... C07D 233/64
[52] U.S. Cl. ................................... 548/343; 568/415
[58] Field of Search ........................................ 548/343

[56] References Cited

U.S. PATENT DOCUMENTS

| | | | |
|---|---|---|---|
| 3,519,637 | 7/1970 | Hoffer | 424/270 X |
| 3,950,353 | 4/1976 | Durant et al. | 424/250 X |
| 4,213,994 | 7/1980 | Gebert et al. | 548/343 X |
| 4,220,654 | 9/1980 | Belhofer et al. | 424/273 R |
| 4,262,126 | 4/1981 | Gilman et al. | 548/193 |
| 4,342,765 | 8/1982 | Jones et al. | 424/249 |

FOREIGN PATENT DOCUMENTS 3640  6/1979  European Pat. Off. ............ 548/193

Primary Examiner—Richard A. Schwartz
Attorney, Agent, or Firm—Charles J. Knuth; Albert E. Frost; Robert K. Blackwood

[57] ABSTRACT

A series of 2-guanidino-4-heteroarylthiazoles, wherein the heteroaryl substituent is selected from thiazolyl, triazolyl, imidazolyl, and 2-alkyl, 2-amino and 2-carboxamido derivatives thereof, are disclosed. The novel compounds have activity as antisecretory agents and histamine $H_2$ antagonists and are useful for the treatment of gastric hyperacidity and peptic ulcers. Also disclosed are pharmaceutical compositions containing the novel compounds of this invention and a method of using the compounds in the treatment of gastric hyperacidity and peptic ulcers. Novel intermediates useful in the preparation of the novel antisecretory compounds are also described.

5 Claims, No Drawings

HALOACETYL IMIDAZOLES

CROSS REFERENCE TO RELATED APPLICATION

This application is a division of application Ser. No. 293,574, filed Aug. 20, 1981, now U.S. Pat. No. 4,374,843, which is a continuation-in-part of U.S. patent application Ser. No. 196,231, filed Oct. 14, 1980, now abandoned.

BACKGROUND OF THE INVENTION

The present invention relates to novel 2-guanidino-4-heteroarylthiazoles having activity as antisecretory agents and histamine $H_2$ antagonists and which are accordingly useful in the prevention and treatment of gastric hyperacidity and peptic ulcers.

Chronic gastric and duodenal ulcers, together known as peptic ulcers, are a common ailment for which a variety of treatments, including dietary measures, drug therapy and surgery, may be employed, depending on the severity of the condition. Particularly valuable therapeutic agents useful for the treatment of gastric hyperacidity and peptic ulcers are the histamine $H_2$-receptor antagonists, which act to block the action of the physiologically active compound histamine at the $H_2$-receptor sites in the animal body and to thereby inhibit the secretion of gastric acid.

SUMMARY OF THE INVENTION

The present invention relates to novel 2-guanidino-4-heteroarylthiazoles useful as histamine-$H_2$ antagonists and as antisecretory agents and which are therefore useful in the treatment of peptic ulcers and other conditions caused or aggravated by gastric hyperacidity. More specifically, the novel compounds of this invention are those of the formula

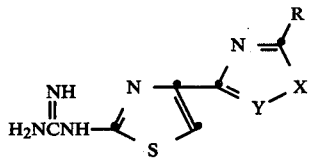

wherein X is S or NH; Y is CH, C.CH$_3$ or N; R is hydrogen, hydroxymethyl, alkyl of 1 to 6 carbon atoms, —(CH$_2$)$_n$Ar, —NH$_2$, —NHR$_1$ or —NHCOR$_1$, wherein R$_1$ is alkyl of 1 to 6 carbon atoms or —(CH$_2$)$_m$Ar; wherein n is an integer from 2 to 4; m is zero or an integer from 1 to 4; and Ar is phenyl or phenyl monosubstituted with chloro, bromo, fluoro, alkyl of 1 to 3 carbon atoms or alkoxy of 1 to 3 carbon atoms; provided that when Y is N, Y is NH and m is other than zero; and when X is S, R is other than hydroxymethyl, alkyl or —(CH$_2$)$_n$Ar.

One group of compounds of interest are those wherein Y is CH and X is S, that is 2-guanidino-4-thiazolyl-thiazole and derivatives thereof. Preferred compounds include those where R is hydrogen, —NH$_2$, —NHCH$_3$ and NHCOCH$_3$.

A further group of compounds of particular interest embraced by the present invention are those wherein Y is CH and X is NH, that is 2-guanidino-4-imidazolyl-thiazole and derivatives thereof. Preferred compounds include those wherein R is hydrogen, hydroxymethyl, methyl, —NH$_2$, —NHCH$_3$ or —NHCOCH$_3$, especially hydrogen, hydroxymethyl, methyl or —NH$_2$.

Another group of compounds of this invention are those wherein Y is C.CH$_3$ and X is NH, that is 2-guanidino-4-(4-methyl-5-imidazolyl)-thiazole and derivatives thereof. Preferred compounds include those wherein R is hydrogen or methyl.

Another group of compounds of the present invention are those wherein Y is N and X is NH, that is 2-guanidino-4-triazolyl-thiazole and derivatives thereof. Preferred compounds include those wherein R is —NH$_2$ or methyl.

Also embraced by the present invention are pharmaceutical compositions comprising a gastric antisecretory effective amount of a compound of formula I, or a pharmaceutically acceptable acid addition salt thereof, together with a pharmaceutically acceptable carrier or diluent. Preferred pharmaceutical compositions are those containing the preferred compounds of formula I as described hereinabove, including those wherein Y is CH, X is S and R is —NH$_2$; Y is CH, X is NH and R is hydrogen, hydroxymethyl, methyl or —NH$_2$; and where Y is N, X is NH and R is —NH$_2$ or methyl.

The present invention also comprises the method of treating gastric hyperacidity in an animal in need of treatment comprising administering to the animal a gastric antisecretory effective amount of a compound of formula I or a pharmaceutically acceptable salt thereof. Preferred compounds for use in this method of treatment are the preferred compounds of formula I as described herein above.

The present invention also includes novel intermediates useful in the preparation of the compounds of formula I. More particularly, such compounds are those of the formula

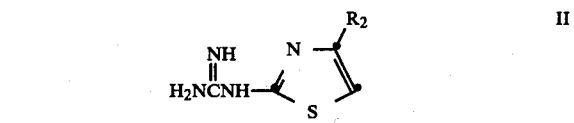

and the acid addition salts thereof, wherein R$_2$ is —COCH(R″)R$_3$ or —CONHR$_4$, wherein R″ is hydrogen or methyl, R$_3$ is halo, N$_3$ or —NH$_2$ and R$_4$ is —NH$_2$ or —NHC(NH)NH$_2$.

Further intermediates useful for the preparation of compounds of formula I are those of the formula

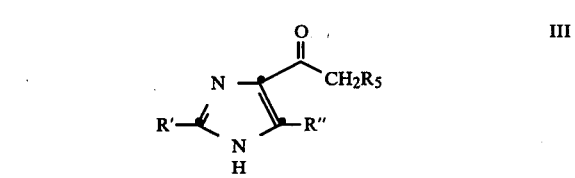

and the acid addition salts thereof, wherein R′ is hydrogen, hydroxymethyl, alkyl of 1 to 6 carbon atoms or —(CH$_2$)$_n$Ar, wherein n and Ar are as previously defined; R″ is hydrogen or methyl; and R$_5$ is halo, preferably chloro or bromo. Preferred intermediates of formula III are those wherein R′ is hydrogen or methyl and R$_5$ is chloro or bromo.

Further intermediates embraced by the present invention are the novel 3-halo-4-n-alkoxy-3-buten-2-ones, wherein the n-alkoxy group has from 1 to 4 carbon atoms, preferably methoxy or ethoxy, especially the compounds where the halo group is chloro or bromo which are useful in the preparation of the intermediates of formula III.

DETAILED DESCRIPTION OF THE INVENTION

The novel compounds of formula I wherein Y is CH or $C.CH_3$ and X is NH or S are prepared from the corresponding novel intermediates of formula II wherein $R_2$ is —COCH(R")$R_3$ and $R_3$ is halo, preferably chloro or bromo, most preferably bromo. Such intermediates where $R_2$ is —COCH$_2R_3$ are prepared from a 1,4-dihalo-2,3-butane-dione, preferably 1,4-dibromo-2,3-butanedione, by the reaction with an excess of a trialkylorthoformate, preferably triethylorthoformate, in the presence of a catalytic amount of a strong acid, such as concentrated sulfuric acid, p-toluene sulfonic acid and the like, at temperature from about 0° C. to about 55° C., preferably from about 15° C. to about 25° C. The 1,4-dihalo-2,2-dialkoxy-3-butanone produced is then reacted with N-amidinothiourea in an organic solvent, such as tetrahydrofuran, dioxane, ether and the like, at a temperature from about 0° C. to about 55° C., preferably from about 20° C. to 50° C., to form 2-guanidino-4-(2-halo-1,1-dialkoxyethyl)thiazole. The latter compound is heated in a hydrogen halide solution, preferably hydrogen bromide, at a temperature from about 0° C. to about 50° C., preferably from about 20° C. to about 30° C. to form the desired 2-halo-1-(2-guanidino-4-thiazolyl)ethanone i.e. the intermediate of formula II, wherein $R_2$ is —COCH$_2R_3$ and $R_3$ is halo, preferably bromo. Similarly, compounds of formula II wherein $R_2$ is —COCH(CH$_3$)$R_3$ may be prepared by the reaction of a 1-halo-2,3-pentanedione with N-amidinothiourea, as previously described, to form 1-(2-guanidino-4-thiazolyl) propanone, which is then reacted with a halogen in aqueous hydrogen halide solution, preferably with bromine in aqueous hydrobromic acid solution, to give the desired intermediates of formula II.

The compounds of formula I wherein Y is CH or $C.CH_3$ and X is S are prepared directly from an appropriate 2-halo-1-(2-guanidino-4-thiazolyl)alkanone intermediate of formula II by reaction with an appropriate compound of the formula RC(S)NH$_2$. For example, reaction of the intermediate 2-halo-1-(2-guanidino-4-thiazolyl)-ethanone with a thiourea or a N-$R_1$-substituted-thiourea yields compounds of formula I wherein Y is CH, X is S and R is NHR$_1$, while reaction with thioformamide provides the compound of formula I wherein Y is CH, X is S and R is hydrogen. The reaction of the 2-halo-1-(2-guanidino-4-thiazolyl)alkanone with the appropriate compound of formula RC(S)NH$_2$ is generally conducted at a temperature from about 0° C. to about 30° C., preferably from about 20° C. to 30° C., in an inert solvent such as dimethylformamide or other polar organic solvents.

Alternatively, the compounds of formula I wherein Y is $C.CH_3$ and X is S may be prepared by reaction of a 4-halo-2,3-pentanedione, preferably 4-bromo-2,3-pentanedione, with an appropriate thioamide of the formula RC(S)NH$_2$ to form a 2-R-4-acetyl-5-methyl-thiazole. These intermediates may be halogenated to the 2-halo-1-(2-R-5-methyl-4-thiazolyl) ethanones, which in turn may be reacted with N-amidinothiourea to afford compounds of formula I where Y is $C.CH_3$ and X is S.

Alternatively, compounds of formula I wherein Y is CH, or $C.CH_3$, X is S and R is —NHR$_1$ where R$_1$ is alkyl or aralkyl may also be prepared by reaction of the corresponding compounds of formula I wherein R is —NH$_2$ with an alkyl or aralkyl halide in the presence of a base. Similarly, the compounds of formula I wherein Y is CH or $C.CH_3$, X is S and R is —NHCOR$_1$ may be prepared by the reaction of the corresponding compound of formula I wherein R is —NH$_2$ by reaction with an appropriate carboxylic acid halide or anhydride.

Compounds of formula I wherein Y is CH or $C.CH_3$ and X is NH may also be prepared from the previously described 2-halo-1-(2-guanidino-4-thiazolyl)alkanone intermediates by first forming the corresponding 2-azido-1-(2-guanidino-4-thiazolyl)alkanone i.e. the novel intermediate of formula II wherein $R_2$ is —COCH(R")$R_3$ and $R_3$ is $N_3$. The latter compound is formed by the reaction of the 2-halo-1-(2-guanidino-4-thiazolyl)alkanone with an alkali metal azide, such as sodium or potassium azide, in a polar organic solvent such as dimethylformamide or other N,N-dialkylamides at a temperature from about 0° C. to about 100° C., preferably from about 60° C. to about 100° C., followed by addition of a base such as an alkali metal hydroxide or an alkali metal carbonate, preferably sodium or potassium carbonate.

For the preparation of compounds of formula I wherein Y is CH or $C.CH_3$, X is NH and R is —NH$_2$ or —NHR$_1$, the 2-azido-1-(2-guanidino-4-thiazolyl)ethanone is first reduced to the corresponding 2-amino compound i.e. the novel intermediate of formula II wherein $R_2$ is —COCH(R")$R_3$ and $R_3$ is —NH$_2$, for example by hydrogenation in the presence of a noble metal catalyst, such as palladium on carbon, or platinum oxide, in an aqueous lower alkyl alcohol solvent, preferably aqueous methanol or ethanol, in the presence of a strong acid, such as concentrated hydrochloric acid, sulfuric acid, p-toluene sulfonic acid and the like, at a temperature from about 15° C. to about 50° C., preferably from about 20° C. to about 35° C. The 2-amino-1-(2-guanidino-4-thiazolyl)alkanone is then reacted with an appropriate cyanamide of the formula H$_2$NCN or R$_1$NHCN, followed by the addition of a base such as an alkali metal hydroxide or carbonate, preferably sodium or potassium carbonate, to provide compounds of formula I wherein Y is CH or $C.CH_3$, X is NH and R is —NH$_2$ or —NHR$_1$, respectively. The N-substituted cyanamides, R$_1$NHCN, used in this reaction can be readily prepared by reaction of the corresponding substituted amine with a cyanogen halide, such as cyanogen bromide or chloride. The reaction of the 2-amino-1-(2-guanidino-4-thiazolyl)alkanone with cyanamide or the appropriate N-substituted cyanamide of the formula R$_1$NHCN is generally effected at a temperature from about 15° C. to about 100° C., preferably from about 70° C. to about 100° C., in aqueous solution at a pH between about 4 and 5, preferably about 4.5.

Alternatively, compounds of formula I wherein Y is CH or $C.CH_3$, X is NH and R is —NHR$_1$ where R$_1$ is alkyl or aralkyl may also be prepared from the corresponding compounds of formula I wherein R is —NH$_2$ by reaction with an alkyl or aralkyl halide in the presence of a base. Further, the compounds of formula I wherein Y is CH or $C.CH_3$, X is NH and R is —NH$_2$ may be reacted with an appropriate carboxylic acid halide or anhydride to form the corresponding compounds of formula I wherein R is —NHCOR$_1$.

Compounds of formula I wherein Y is CH or $C.CH_3$, X is NH and R is hydrogen, hydroxymethyl, alkyl or —(CH$_2$)$_n$Ar are prepared from the 2-amino-1-(2- guanidino-4-thiazolyl)alkanone by reaction with an alkyl carboximidate of the formula $RC(NH)OR_6$, where $R_6$ is alkyl of 1 to 3 carbon atoms, preferably methyl or ethyl, or an acid addition salt thereof, for example the hydrogen halide salt, preferably the hydrochloride or hydrobromide salt. The reaction is generally conducted in a lower alkyl alcohol solvent, preferably methanol or ethanol, at a temperature from about 0° C. to 70° C. The compound so formed is then converted to the desired compound of formula I wherein Y is CH, X is NH and R is hydrogen or alkyl by heating in the presence of an acid, such as hydrochloric acid, sulfuric acid, p-toluene sulfonic acid and the like, followed by the addition of a base such as an alkali metal hydroxide or carbonate, preferably sodium or potassium carbonate. Alternatively, the 2-azido-1-(2-guanidino-4-thiazolyl)alkanone may be reacted with a trialkylorthoformate to form the corresponding 1,1-dialkoxy derivative, which is then reduced to the 2-amino compound and reacted with an alkyl carboximidate, as previously described.

The compounds of formula I wherein Y is N and X is NH may be prepared from 2-guanidino-4-thiazole carboxylic acid hydrazide i.e. the novel intermediate of formula II wherein $R_2$ is $-CONHR_4$ and $R_4$ is $-NH_2$. This intermediate is prepared by the reaction of an alkyl halopyruvate, preferably ethyl bromopyruvate, with N-amidinothiourea in an organic solvent, such as a lower alkyl alcohol of 1 to 4 carbon atoms, preferably methanol or ethanol, at a temperature from about 0° C. to about 100° C., preferably at the reflux temperature of alcohol solvent, to form a 2-guanidino-4-thiazole carboxylic acid alkyl ester. The latter is then reacted with hydrazine in a lower alcohol solvent, preferably absolute ethanol, at a temperature from about 0° C. to about 100° C. preferably at the reflux temperature of the alcohol solvent, to form the desired 2-guanidino-4-thiazole carboxylic acid hydrazide.

The hydrazide derivative formed as described above is reacted with an alkyl carboximidate of the formula $RC(NH)OR_6$, where $R_6$ is alkyl of 1 to 3 carbon atoms, preferably methyl or ethyl, or an acid addition salt thereof, preferably a hydrohalide such as the hydrochloride or hydrobromide salt, to form the corresponding 2-guanidino-4-thiazole carboxylic acid 2-carboximinohydrazide. The reaction is conducted in an inert organic solvent, preferably a lower alkyl alcohol, such as methanol or ethanol, in the presence of a base, such as an alkali metal alkoxide, preferably sodium or potassium ethoxide, at a temperature from about 10° C. to about 100° C., preferably from about 20° C. to 75° C. The 2-guanidino-4-carboxylic acid 2-carboximinohydrazide is then heated at a temperature from about 75° C., to about 110° C., preferably from about 90° C. to 100° C., in concentrated ammonia solution to form the desired compound of formula I wherein Y is N and X is NH.

The compounds of formula I wherein Y is N, X is NH and R is $-NH_2$ may be formed from the 2-guanidino-4-thiazole carboxylic acid hydrazide previously described by reaction with 2-methylthiopseudourea $H_2NC(SCH_3)NH$, or an acid addition salt thereof, such as the hydrohalide, preferably the hydrochloride or hydrobromide, or the hemisulfate, to form 2-guanidino-4-thiazole carboxylic acid 2-amidinohydrazide i.e. the novel intermediate of formula II wherein $R_2$ is $-CONHR_4$ and $R_4$ is $-NHC(NH)NH_2$. The reaction is generally conducted in an organic solvent such as dimethylsulfoxide at a temperature from about 150° C. to about 225° C., preferably about 180° C. to about 200° C.

The product is then heated at a temperature from about 75° C. to about 110° C., preferably about 90° C. to about 100° C., in concentrated ammonia solution to form the desired compound of formula I wherein Y is N, X is NH and R is $-NH_2$.

The compounds of formula I where Y is N, X is NH and R is $-NH_2$ may be reacted with an appropriate alkyl or aralkyl halide in the presence of a base to form the corresponding compounds of formula I wherein R is $-NHR_1$ where $R_1$ is alkyl or aralkyl. Similarly, such compounds where R is $-NH_2$ may be converted to the corresponding compounds where R is $-NHCOR_1$ by reaction with an appropriate carboxylic acid halide or anhydride.

An alternative method of preparing the compounds of formula I wherein R is hydrogen, alkyl or $(CH_2)_nAr$ is by the reaction of an intermediate of the formula

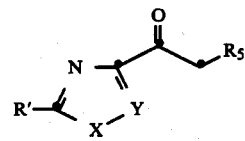

IV wherein R' is hydrogen, hydroxymethyl, alkyl or $-(CH_2)_nAr$, where n and Ar are as previously defined, and $R_5$ is halo, with N-amidinothiourea in an organic solvent such as tetrahydrofuran, ether, a lower alkyl alcohol such as methanol or ethanol and the like at a temperature from about 0° C. to about 75° C. This method of preparation is of particular interest for the preparation of compounds of formula I wherein X is NH and Y is CH or $C.CH_3$. The intermediates of formula IV wherein X is NH and Y is CH or $C.CH_3$ (i.e. the compounds of formula III as previously described) may be prepared by halogenation of the corresponding 2-R'-5-R"-4-acetyl-imidazole where R" is hydrogen or methyl, for example by reaction with a halogen in an aqueous hydrogen halide solution, preferably with bromine in aqueous hydrobromic acid.

The 2-R'-5-R"-4-acetyl imidazole for use in this reaction may be prepared by irradiation of 1-acetyl-2-R'-5-R"-imidazole with ultra-violet light. Alternatively, 2-R'-4-acetyl-imidazoles may be prepared by reaction of a 3-halo-4-n-alkoxy-3-buten-2-one, especially the 3-chloro- or 3-bromo-compound, with an appropriate R'-substituted amidine of the formula $R'C(NH_2)NH$ or a salt thereof in the presence of a base such as a trialkylamine, preferably triethylamine, in an organic solvent such as acetone, tetrahydrofuran, dioxane and the like, at a temperature from about 0° C. to about 100° C., preferably at reflux temperature in tetrahydrofuran.

The 3-halo-4-n-alkoxy-3-buten-2-one starting materials may be prepared from the known 3-halo-4-hydroxy-3-buten-2-one by reaction with a dialkylsulfate or diazoalkane in, for example, aqueous tetrahydrofuran or dioxane, in the presence of a weak base such as an alkali metal bicarbonate at a temperature from about 0° C. to about 60° C., preferably from about 15° C. to 30° C. Alternatively, the 3-halo-4-n-alkoxy-3-buten-2-one may be prepared by heating a 3-halo-4-hydroxy-3-buten-2-one at reflux with an appropriate n-alkanol, for example in toluene solution.

The preparation of corresponding intermediates of formula IV for the preparation of other compounds of formula I i.e. having other X and Y groups, may be prepared by reactions analogous to those described hereinabove by the use of appropriately substituted starting materials.

The pharmaceutically acceptable acid addition salts of the novel compounds of formula I are also embraced by the present invention. The salts are readily prepared by contacting the free base with an appropriate mineral or organic acid in either aqueous solution or in a suitable organic solvent. The solid salt may then be obtained by precipitation. or by evaporation of the solvent. The pharmaceutically acceptable acid addition salts of this invention include, but are not limited to, the hydrochloride, sulfate, bisulfate, mesylate, nitrate, phosphate, acetate, lactate, maleate, fumarate, citrate, tartrate, succinate, gluconate and the like. Preferred salts are the hydrochloride and dihydrochloride. If desired, the compounds of formula I as the free base may be formed from the acid addition salts thereof by treatment with an appropriate base followed by extraction of the free base with a suitable organic solvent.

The compounds of formula I and the pharmaceutically acceptable acid addition salts thereof have activity as antisecretory agents and histamine $H_2$ antagonists and accordingly are of therapeutic value in the treatment of gastric hyperacidity and peptic ulcers. For the purposes of the present specification and claims hereof the term treatment of gastric hyperacidity is meant to include the treatment of peptic ulcers and other such conditions caused by, or aggravated, by the secretion of gastric acid. The compounds may be administered to a subject in need of treatment by a variety of conventional routes of administration including orally and parenterally. Preferably, the compounds are administered orally. In general, these compounds will be administered orally at doses between about 0.1 to 20 mg/kg body weight of the subject to be treated per day, preferably from about 0.2 to 2.5 mg/kg per day. If parenteral administration is desired, then these compounds can be given at doses between about 0.1 and 1.0 mg/kg body weight of the subject to be treated per day. However, some variation in dosage will necessarily occur depending upon the condition of the subject being treated and the particular compound employed.

The compound may be administered alone or in combination with pharmaceutically acceptable carriers or diluents, in either single or multiple doses. Suitable pharmaceutical carriers include inert diluents or fillers, sterile aqueous solutions and various organic solvents. The pharmaceutical compositions formed by combining the novel compounds of formula I or salts thereof and pharmaceutically acceptable carriers are readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients, such as sodium citrate, may be employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matters or dyes and, if desired, emulsifying agents or suspending agents, together with diluents such as water, ethanol, propylene glycol, glycerin, or combinations thereof.

Preferably, the novel compounds of this invention are administered orally in unit dosage form, i.e. as a single physically discrete dosage unit containing an appropriate amount of the active compound in combination with a pharmaceutically acceptable carrier or diluent. Examples of such unit dosage forms are tablets or capsules containing from about 5 to 1,000 mg of the active ingredient, the compound of formula I comprising from about 10% to 90% of the total weight of the dosage unit.

For parenteral administration, solutions of the compounds of formula I in sterile aqueous solutions, for example aqueous propylene glycol, sodium chloride, dextrose or sodium bicarbonate solutions may be employed. Such solutions should be suitably buffered if necessary and the liquid diluent first rendered isotonic with sufficient saline or glucose. The preparation of suitable sterile liquid media for parenteral administration will be well known to those skilled in the art.

The activity of the compounds of the present invention as antisecretory agents and histamine-$H_2$ antagonists may be determined by standard pharmacological tests, including for example (1) measuring their ability to antagonize the actions of histamine which are not blocked by an antihistamine such as mepyramine and (2) measuring their ability to inhibit gastric acid secretion in the stomachs of Heidenhain pouch dogs that had previously been treated with pentagastrin in order to stimulate the secretion of gastric acid.

The present invention is illustrated by the following examples. However, it should be understood that the invention is not limited to the specific details of these examples. All temperatures are in degrees centigrade.

EXAMPLE 1

1,4-Dibromo-2,2-diethoxy-3-butanone

A mixture of 40 g (0.164 mol) of 1,4-dibromo-2,3-butanedione, 60 ml (0.36 M) of triethylorthoformate, and 2 ml of concentrated sulfuric acid was stirred at room temperature for 14 hours, then diluted with 600 ml of chloroform, and washed successively with 100 ml portions of water, 0.5 N hydrochloric acid and saturated sodium chloride solution. The organic solution was dried over anhydrous sodium sulfate filtered, and evaporated leaving an oil. The oil was taken up into 300 ml of hexane and filtered to remove some insoluble material. The hexane filtrate was cooled in a dry-ice-/acetone bath, and the resulting precipitate was collected by filtration and dried to give 44 g (84%) of 1,4-dibromo-2,2-diethoxy-3-butanone as a white crystalline solid, mp 40°–41.5°; nmr (CDCl$_3$) ($\delta$): 4.50 (s, 2H); 3.6–3.2 (m, 6H); 1.22 (t, 6H).

EXAMPLE 2

2-Guanidino-4-(4-bromo-1,1-diethoxyethyl)thiazole

A mixture of 25.5 g (80 mmol) of 1,4-dibromo-2,2-diethoxy-3-butanone, 11.8 g (100 mmol) of N-amidinothiourea, and 150 ml of tetrahydrofuran was heated at reflux for 3 hours. The mixture was filtered to remove some insoluble solid, and the filtrate was concentrated. The residue was triturated with 200 ml of saturated sodium bicarbonate, then extracted four times with a total of 500 ml of ethyl acetate. The combined ethyl acetate extracts were dried over sodium sulfate, filtered and evaporated leaving a solid. Recrystallization from 250 ml of acetonitrile, after decolorization with charcoal, afforded 9.7 g (36%) of 2-guanidino-4-(2-bromo-1,1-diethoxyethyl)thiazole as a white solid, mp 157°–158°; calcd. for $C_{10}H_{17}N_4O_2SBr$: C, 35.62; H, 5.08; N, 16.61; Br, 23.69; S, 9.51; found: C, 35.60; H, 4.97; N, 16.99; Br, 23.75; S, 9.59.

EXAMPLE 3

2-Bromo-1-(2-guanidino-4-thiazolyl)ethanone hydrobromide

A mixture of 9.5 g (28 mmol) of 2-guanidino-4-(2-bromo-1,1-diethoxyethyl)thiazole in 50 ml of 48% hydrobromic acid was stirred at room temperature for 15 hours. The mixture was evaporated to complete dryness to afford 10.1 g (100%) of 2-bromo-1-(2-guanidino-4-thiazolyl)ethanone hydrobromide mp 247° (dec). This material could be converted to the free base by triturating with saturated sodium bicarbonate, stirring for 15 minutes, filtering the solid, and drying it under vacuum. In this way, 3.0 g of the hydrobromide salt was converted to 1.7 g (88%) of the free base, mp 210° (dec); nmr (DMSO-$d_6$ ($\delta$): 7.84 (s, 1H); 6.92 (s, 4H); 4.78 (s, 2H).

EXAMPLE 4

2-Guanidino-4-(2-amino-4-thiazolyl)thiazole dihydrobromide

A solution of 688 mg (2.0 mmol) of 2-bromo-1-(2-guanidino-4-thiazolyl)ethanone hydrobromide and 183 mg of thiourea in 5 ml of dimethylformamide was stirred at room temperature. After a short time, a solid began to precipitate. After a total of four hours, the solid was collected by filtration, washed with ethyl acetate, and dried, thereby affording 595 mg (74%) of 2-guanidino-4-(2-amino-4-thiazolyl)thiazole dihydrobromide as a white powder; mp 320° (dec); mass spectrum parent of 240. This material could be converted to its free base by triturating with saturated sodium bicarbonate solution, stirring for 15 minutes, filtering the solid, and drying it under vacuum. In this way 2-guanidino-4-(2-amino-4-thiazolyl)thiazole was obtained as a crystalline solid, mp 274°. Calcd. for $C_7H_8N_6S_2$: C, 34.99; H, 3.36; N, 34.97; found: C, 34.94; H, 3.41; N, 34.80.

EXAMPLE 5

2-Guanidino-4-(4-thiazolyl)thiazole

A mixture of 1.8 g (5.2 mmol) of 2-bromo-1-(2-guanidino-4-thiazolyl)ethanone hydrobromide, 0.34 g (5.5 mmol) of thioformamide, and 10 ml of dimethylformamide was stirred at room temperature for 2 hours. The mixture was concentrated and the residue was triturated with acetonitrile. The resulting precipitate was collected by filtration, washed with acetonitrile, and dried to afford 1.74 g (85%) of 2-guanidino-4-(4-thiazolyl)thiazole dihydrobromide. This was dissolved in 10 ml of water, and 1 ml of saturated sodium bicarbonate solution was added. The resulting precipitate was collected by filtration, washed well with water, then acetonitrile, then dried in vacuo to afford 1.17 g of 2-guanidino-4-(4-thiazoyl)thiazole as a white solid, mp 220°–222°; nmr (DMSO-$d_6$) ($\delta$): 8.96 (s, 1H); 7.96 (s, 1H); 7.18 (s, 1H); 7.0 (b, 4H); calcd. for $C_7H_7N_5S_2$: C, 37.32; H, 3.13; N, 31.09; found: 36.94; H, 3.52; N, 29.74.

EXAMPLE 6

2-Guanidino-4-(2-N-methylamino-4-thiazoyl)thiazole

A mixture of 1.77 g (5.14 mmol) of 2-bromo-1-(2-guanidino-4-thiazoyl)ethanone hydrobromide, 0.49 g (5.5 mmol) of N-methylthiourea, and 10 ml of dimethylformamide was stirred at room temperature for 18 hours. The mixture was concentrated and the residue was triturated with a small amount of acetonitrile. The crude solid was collected by filtration, then dissolved in water. The aqueous solution was made basic with saturated sodium bicarbonate solution and the resulting precipitate was collected by filtration and allowed to dry. Recrystallization from ethanol/water afforded 0.70 g (54%) of 2-guanidino-4-(2-N-methylamino-4-thiazoyl)thiazole as a white solid, mp 267°; nmr (DMSO-$d_6$($\delta$): 7.44 (q, 1H); 7.0–6.9 (s+s+b, 6H); 2.85 (t, 3H); calcd. for $C_8H_{10}N_6S_2$: C, 37.77; H, 3.96; N, 33.05; found: C, 38.01; H, 4.47: N, 32.84.

EXAMPLE 7

2-Guanidino-4-(2-N-acetylamino-4-thiazoyl)thiazole

A mixture of 1.77 g (5.14 mmol) of 2-bromo-1-(2-guanidino-4-thiazoyl)ethanone hydrobromide, 0.65 g (5.5 mmol) of N-acetylthiourea, and 10 ml of dimethylformamide was stirred at room temperature for 18 hours. The mixture was concentrated and the residue triturated with acetonitrile. The resulting solid was collected by filtration, then added to 50 ml of saturated sodium bicarbonate solution and stirred for 1 hour. The solid was collected by filtration and allowed to dry. Recrystallization from ethanol/water afforded 1.0 g (68%) of 2-guanidino-4-(2-N-acetylamino-4-thiazoyl)-thiazole as a white solid, mp 288°; nmr (DMSO-$d_6$) ($\delta$): 7.40 (s, 1H); 7.0–6.9 (b, 5h); 3.2 (b, 1H); 2.22 (s, 3H); calcd. for $C_9H_{10}N_6OS_2$: C, 38.28; H, 3.57; N, 29.77; found: C, 38.13; H, 4.07; N, 29.41.

EXAMPLE 8

2-Guanidino-4-thiazole carboxylic acid ethyl ester 111.2 g (0.94 mol) of 2-amidinothiourea was dissolved in 1 liter of refluxing ethanol. To the refluxing solution was rapidly added over a 10 minute period 200 g (1.02 mol) of ethyl bromopyruvate. After 2 hours of reflux an additional 20 g (0.1 mol) of ethyl bromopyruvate was added and reflux was continued for an additional 2 hours. The reaction was cooled to 10° and concentrated ammonium hydroxide solution was added to raise the pH to 10. A solid formed and was collected by filtration, washed twice with ether and dried in vacuo to give 176.4 g (88%) of 2-guanidino-4-thiazole carboxylic acid ethyl ester, mp 229°–230° (dec.).

EXAMPLE 9

2-Guanidino-4-thiazole carboxylic acid hydrazide 16.7 g (0.0779 mol) of 2-guanidino-4-thiazole carboxylic acid ethyl ester was combined with 25 ml (0.514 mol) of hydrazine hydrate in 200 ml absolute ethanol. The slurry was heated to reflux. After 1.5 hour reflux a solid began to form from the clear solution. After 2 hours reflux the reaction slurry was cooled and the resulting solid was collected by filtration and was washed with isopropyl alcohol and ether to give 12.8 g (82%) 2 guanidino-4-thiazole carboxylic acid hydrazide, mp 247° (dec.).

EXAMPLE 10

2-Guanidino-4-thiazole carboxylic acid 2-amidinohydrazide hemisulfate 17.9 g (0.089 mol) of 2 guanidino-4-thiazole carboxylic acid hydrazide was combined with 24.9 g of 2-methyl-2-thiopseudourea sulfate (0.089 mol) and heated rapidly to reflux in 125 ml dimethylsulfoxide. The reactants dissolved and within 5 minutes reflux a heavy precipitate formed. Reflux was continued for a total of 30 minutes. The reaction was cooled and the resulting heavy precipitate was isolated by filtration and washed with a small portion of dimethylsulfoxide followed by washing with isopropyl alcohol and ether. The resulting solid was dried in vacuo to give 34.6 g of 2-guanidino-4-thiazole carboxylic acid 2-amidinohydrazide containing some occluded dimethylsulfoxide.

EXAMPLE 11

2-Guanidino-4-(3-amino-5-1,2,4-triazolyl)thiazole 29.1 g (0.1 mol) of 2-guanidino-4-thiazole carboxylic acid 2-amidino hydrazide hemisulfate was heated to boiling with 250 ml concentrated ammonium hydroxide. Additional ammonium hydroxide was added to replace the volume lost due to loss of ammonia. After 8 hours heating, boiling was continued until the pH was below 8.0 and the mixture was allowed to cool. The resulting solid was collected by filtration, washed with a small portion of water, decolorized with charcoal, recrystallized from water and dried in vacuo to give 10.8 g (48%) of 2-guanidino-4-(3-amino-5-1,2,4-triazolyl)thiazole, mp 173°–5°. nmr (DMSO-D$_6$) ($\delta$): 7.07 (s, 1H); 6.93 (broad s, 4H); 5.53 (broad s, 2H); Calcd. for C$_6$H$_8$N$_8$S: C, 32.14; H, 3.60; N, 49.97; found: C, 32.13; H, 3.70; N, 50.15.

EXAMPLE 12

2-Guanidino-4-thiazole carboxylic acid 2-acetiminohydrazide 37.1 g (0.3 mol) of ethyl acetimidate hydrochloride was dissolved in 200 ml absolute ethanol. A solution of sodium ethoxide (6.9 g (0.3 mol) sodium in 300 ml absolute ethanol) was added. The resulting precipitate of sodium chloride was removed by filtration and to the clear filtrate was added 20.0 g (0.1 mol) of 2-guanidino-4-thiazole carboxylic acid hydrazide. The slurry was stirred at 25° for 60 hours, during which time complete dissolution occurred. The clear, pale orange solution was concentrated in vacuo to a soft solid which was triturated in 10:1 ethyl acetate-ethanol to give 24.0 g (88%) of crude 2-guanidino-4-thiazole carboxylic acid 2-acetiminohydrazide, with a broad melting point, 150° to 178° (dec.).

EXAMPLE 13

2-Guanidino-4-(3-methyl-5-1,2,4-triazolyl)thiazole hemihydrate 23.0 g (0.095 mol) of 2-guanidino-4-thiazole carboxylic acid 2-acetiminohydrazide was heated to boiling with 200 ml concentrated ammonium hydroxide solution. Additional ammonium hydroxide was added to replace the volume lost due to loss of ammonia. After 7 hours heating, boiling was continued until the pH was below 8.0 and the mixture was allowed to cool. The resulting solid was collected by filtration, washed with a small portion of water and then dried (110°/0.1 mm Hg) for 24 hours to give 8.6 g (39%) 2-guanidino-4-(3-methyl-5-(1,2,4-triazolyl)thiazole hemihydrate mp 185° (loss of H$_2$O), 260° (dec.). nmr (DMSO-d$_6$) ($\delta$): 7.22 (s, 1H); 6.90 (broad s, 4H), 3.50 (broad s, 1H—H$_2$O); 2.32 (s, 3H); Calcd. for C$_7$H$_9$N$_7$S.$\frac{1}{2}$H$_2$O: C, 36.19; H, 4.34; N, 42.22; found: C, 36.43; H, 4.29; N, 42.17.

EXAMPLE 14

2-Guanidino-4-thiazole carboxylic acid 2-butyriminohydrazide 2.90 g (14.48 mol) of 2-guanidino-4-thiazole carboxylic acid hydrazide in 50 ml dry ethanol was slurried with 29.1 mmol of ethyl butyrimidate (prepared from 4.41 g (29.1 mmol) of ethylbutyrimidate hydrochloride) for 5 days at 25°. The slurry was filtered and washed with ethanol and ether and dried to give 3.071 g (78%) of 2-guanidino-4-thiazole carboxylic acid 2-butyriminohydrazide.

EXAMPLE 15

2-Guanidino-4-(3-propyl-5-1,2,4-triaziolyl)thiazole hemihydrate 2.547 g (9.5 mmol) of 2-guanidino-4-thiazole carboxylic acid 2-butyriminohydrazide was heated at reflux in 50 ml water for 2 hours. The reaction was cooled and the resultant solid was recrystallized from 150 ml of a 4:1 water:ethanol solution to give 1.119 g (47%) of 2-guanidino-4-(3-propyl-5-1,2,4-triazolyl)thiazole hemihydrate, mp 268°–270° (dec.). nmr (DMSO-d$_6$) ($\delta$): 13.68 (broad s, 1H); 7.18 (s, 1H); 6.90 (broad s, 4H); 2.64 (t, 2H); 1.70 (m, 2H); 0.90 (t, 3H); Calcd. for C$_9$H$_{13}$N$_7$S.$\frac{1}{2}$H$_2$O: C, 41.52; H, 5.42; N, 37.66; found: C, 41.81; H, 5.50; N, 38.10.

EXAMPLE 16

2-Guanidino-4-thiazole carboxylic acid-2-propioniminohydrazide 2.90 g (14.48 mmol) of 2-guanidino-4-thiazole carboxylic acid hydrazide in 50 ml dry ethanol was slurried with 29.1 mmol of ethyl propionimidate (prepared from 4.0 g (29.1 mmol) of ethyl propionimidate hydrochloride) for 5 days at 25°. The slurry was filtered and the resulting solid was dried for 2 hours at 60° in vacuo to give 2.802 g (75%) of 2-guanidino-4-thiazole carboxylic acid 2-propioniminohydrazide.

EXAMPLE 17

2-Guanidino-4-(3-ethyl-5-1,24-triazolyl)thiazole 2.726 g (10.7 mmol) of 2-guanidino-4-thiazole carboxylic acid 2-propioniminohydrazide was heated at reflux in 50 ml water for 2 hours. On cooling a solid precipitated. This was treated with 200 ml boiling water, a small quantity of insoluble material was removed and the solvent was cooled to afford a white solid. Two additional recrystallizations from water gave 1.048 g (41%) of 2-guanidino-4-(3-ethyl-5-1,2,4-triazolyl)-thiazole, mp 251°–7° (dec.). nmr (DMSO-d$_6$) ($\delta$): 13.80 (broad s, 1H); 7.27 (s, 1H); 6.95 (broad s, 4H); 2.70 (q, 2H); 1.25 (t, 3H); Calcd. for C$_8$H$_{11}$N$_7$S: C, 40.49; H, 4.67; N, 41.32; found: C, 40.61; H, 4.60; N, 40.50.

EXAMPLE 18

2-Azido-1-(2-guanidino-4-thiazolyl)ethanone

A mixture of 50 g (0.14 mol) of 2-bromo-1-(2-guanidino-4-thiazolyl)ethanone hydrobromide, 23.6 g (0.36 mol) of sodium azide, and 250 ml of dimethylformamide was stirred at room temperature for 1.5 hours. The mixture was poured into 1.5 liters of water, and the aqueous solution was made basic with solid sodium carbonate. The resulting precipitate was filtered, washed well with water, and dried, thereby affording 30.6 g (93%) of 2-azido-1-(2-guanidino-4-thiazolyl)ethanone as a light brown crystalline solid, mp 177° (dec). Analytically pure material can be prepared by recrystallization from absolute ethanol: Calcd. for $C_6H_7N_7OS$: C, 32.00; H, 3.13; N, 43.53; S. 14.24; found: C, 32.22; H, 3.43; N, 41.93; S, 13.97.

EXAMPLE 19

2-Amino-1-(2-guanidino-4-thiazolyl)ethanone.dihydrochloride

A mixture of 12.0 g (53 mmol) of 2-azido-1-(2-guanidino-4-thiazolyl)ethanone, 1.0 g of 10% palladium on carbon, 100 ml of ethanol, 50 ml of water, and 20 ml of concentrated hydrochloric acid was hydrogenated at 3 atm. and room temperature for 1 hour. At this point another 50 ml of water and 300 mg of 10% palladium on carbon was added to the mixture and hydrogenation was continued at 3 atm for another 0.75 hour. The mixture was diluted with 200 ml of water, filtered to remove the catalyst, and the filtrate concentrated leaving 13.1 g (92%) of 2-amino-1-(2-guanidino-4-thiazolyl)ethanone dihydrochloride as a white powder mp>270°. nmr (DMSO-$d_6$) ($\delta$): 8.58 (b, 4H) 8.44 (s, 1H); 4.58 (b, 4H).

EXAMPLE 20

2-Guanidino-4-(2-amino-4-imidazolyl)thiazole

A mixture of 43 g (0.15 mol) of 2-amino-1-(2-guanidino-4-thiazolyl)ethanone dihydrochlorde, 12.6 g (0.30 mol) of cyanamide, and 400 ml of water was brought to pH 4.5 by the dropwise addition of 20% sodium hydroxide solution. The mixture was heated at 50°-60° for 16 hours. The mixture was cooled, made basic with aqueous sodium carbonate solution and the resulting precipitate was collected by filtration, then washed successively with cold water, acetone, and ether. The dried solid was purified by dissolving in a minimum of dimethylformamide, then slowly adding ethyl acetate. Initially tarry material precipitated which was removed by decanting. Further addition of ethyl acetate afforded 16 g of a tan solid. This was again purified by the dimethylformamide-ethyl acetate procedure described above to give 12 g of a tan solid. Recrystallization of this material from methanol/water afforded analytically pure title compound as tan needles, mp 267° (dec). Calcd. for $C_7H_9N_7S$: C, 37.66; H, 4.06; N, 43.91; S, 14.36; found: C, 37.81; H, 4.31; N, 43.76.

EXAMPLE 21

2-Guanidino-4-(2-N-methylamino-4-imidazoyl)thiazole dihydrochloride

A mixture of 2.0 g (7.3 mmol) of 2-amino-1-(2-guanidino-4-thiazolyl)ethanone dihydrochloride, 0.62 g (11 mmol) of N-methylcyanamide, and 10 ml of water was brought to pH 4.5 by the dropwise addition of 20% sodium hydroxide solution. The mixture was heated at 50° for 16 hours. The mixture was cooled, made basic with aqueous sodium carbonate solution and the resulting precipitate was collected by filtration, then washed successively with cold water, acetone, and acetonitrile. The crude solid was converted to its dihydrochloride salt by dissolving it in a minimum amount of saturated methanolic hydrogen chloride, then slowly adding ether. Initially tar precipitated and this was removed by decanting. Further addition of ether resulted in the precipitation of a crystalline solid which was filtered and dried. Recrystallization from methanol/ether afford 190 mg (10%) of the pure title compound, mp 280°; nmr (DMSO-$d_6$) ($\delta$): (free base) 6.86 (b, 5H); 6.77 (s, 1H); 6.45 (s, 1H); 5.60 (b) (1H); 2.68 (d, 3H); calcd. for $C_8H_{11}N_7.2HCl.H_2O$: C, 29.27; H, 4.61; N, 29.87; found: C, 30.01; H, 4.81; N, 29.78.

EXAMPLE 22

2-Guanidino-4-(2-N-ethylamino-4-imidazoyl)thiazole dihydrochloride

A mixture of 4.0 g (15 mmol) of 2-amino-1-(2-guanidino-4-thiazolyl)ethanone dihydrochloride, 1.54 g (22 mmol) of N-ethylcyanamide, and 20 ml of water was brought to pH 4.5 by the dropwise addition of 20% sodium hydroxide solution. The mixture was heated at 50° for 16 hours. The mixture was cooled, made basic with aqueous sodium carbonate solution and the resulting precipitate was collected by filtration and washed successively with cold water, and acetone. The crude solid was converted to its dihydrochloride salt by dissolving it in a minimum about of saturated ethanolic hydrogen chloride, filtering away insolubles, then slowly adding ether. The resulting precipitate was collected by filtration, washed with ether and dried. Recrystallization from ethanol/ether afforded 0.46 g (10%) of the title compound mp 235°; nmr (DMSO-$d_6$) ($\delta$): 8.42 (b, 5H); 7.99 (t, 1H); 7.87 (s, 1H); 7.65 (s, 1H); 3.43 (m, 2H); 1.19 (t, 3H); calcd. for $C_9H_{13}N_7S.2HCl.H_2O$: C, 31.58; H, 4.71; N, 28.65; found: C, 31.11; H, 5.38; N, 27.79.

EXAMPLE 23

2-Guanidino-4-(2-N-n-propylamino-4-imidazoyl)thiazole dihydrochloride

A mixture of 2.0 g (7.3 mmol) of 2-amino-1-(2-guanidino-4-thiazolyl)ethanone dihydrochloride. 0.92 g (11 mmol) of N-n-propylcyanamide, and 20 ml of water was brought to pH 4.5 by the dropwise addition of 20% sodium hydroxide solution. The mixture was heated at 50° for 16 hours, then cooled, made basic with aqueous sodium carbonate solution and filtered to remove some insoluble material. The filtrate was concentrated and the residue was triturated with 50 ml of ethanol and filtered to remove insoluble material. Concentration of the filtrate afforded a crude solid which was converted to its dihydrochloride salt by dissolving in saturated ethanolic hydrogen chloride, filtering away some insoluble material, and diluting the filtrate with ether. The resulting precipitate was filtered, washed with ether and dried. Recrystallization from ethanol/ether afforded 180 mg (7%) of the pure title compound, mp 227°-229°; nmr (DMSO-$d_6$) ($\delta$): 8.40 (b, 6H); 7.86 (s, 1H); 7.64 (s, 1H); 3.40 (m, 2H); 1.62 (m, 2H); 0.09 (t, 3H); calcd. for $C_{10}H_{15}N_7S.2HCl.H_2O$: C, 33.71; H, 5.38; N, 27.52; found: C, 33.75; H, 5.03; N, 26.41.

EXAMPLE 24

2-Guanidino-4-(2-N-i-propylamino-4-imidazoyl)-thiazole dihydrochloride

A mixture of 2.0 g (7.3 mmol) of 2-amino-1-(2-guanidino-4-thiazolyl)ethanone dihydrochloride, 0.92 g (11 mmol) of N-i-propylcyanamide, and 20 ml of water was brought to pH 4.5 by the dropwise addition of 20% sodium hydroxide solution. The mixture was heated at 60° for 16 hours. Another 0.30 g (3.7 mmol) of N-i-propylcyanamide was added and the mixture was heated at 110° for 3 hours. The mixture was made basic with aqueous sodium carbonate solution and filtered to remove some insoluble material. The filtrate was concentrated and the residue was triturated with 50 ml of ethanol and filtered to remove inorganics. Concentration of the filtrate afforded a crude solid which was converted to its dihydrochloride salt by dissolving in saturated ethanolic hydrogen chloride, filtering away insoluble material, and diluting the filtrate with ether. The resulting precipitate was filtered, washed with ether and dried. Recrystallization from ethanol/ether afforded 0.34 g (13%) of the pure title compound, mp 138°; nmr (DMSO-d$_6$) ($\delta$): 8.39 (b, 6H); 7.82 (s, 1H); 7.59 (s, 1H); 3.10 (m, 1H); 1.05 (d, 6H): calcd. for $C_{10}H_{15}N_7S \cdot 2HCl \cdot H_2O$: C, 33.71; H, 5.38; N, 27.52; found: C, 33.71; H, 5.97; N, 26.15.

EXAMPLE 25

2-Guanidino-4-(2-N-n-butylamino-4-imidazoyl)thiazole dihydrochloride

A mixture of 2.0 g (7.3 mmol) of 2-amino-1-(2-guanidino-4-thiazoyl)ethanone dihydrochloride, 1.08 g (11 mmol) of N-n-butylcyanamide; and 20 ml sodium hydroxide solution. The mixture was heated at reflux for 60 hours, then cooled, made basic with aqueous sodium carbonate solution, then concentrated. The solid residue was triturated with methanol, filtered to remove insolubles, and the filtrate concentrated leaving an oil. The oil was taken up in 20 ml of ethanolic hydrogen chloride, filtered again to remove insolubles, and the filtrate was diluted with ether. The resulting precipitate was collected by filtration, washed with ether, and dried in vacuo to afford 0.25 g (10%) of 2-quanidino-4-(2-N-n-butylamino-4-imidazoyl)thiazole dihydrochloride mp 224°–228°; nmr (DMSO-d$_6$) ($\delta$): 8.40 (b, 6H); 7.82 (s, 1H); 7.60 (s, 1H); 3.40 (m, 2H); 1.8–1.3 (m, 4H); 0.97 (t, 3H).

EXAMPLE 26

2-Guanidino-4-(2-N-benzylamino-4-imidazoyl)thiazole dihydrochloride

A mixture of 2.0 g (7.3 mmol) of 2-amino-1-(2-guanidino-4-thiazolyl)ethanone dihydrochloride, 1.45 g (11 mmol) of N-benzylcyanamide, and 20 ml of water was brought to pH 4.5 by the dropwise addition of 20% sodium hydroxide solution. The mixture was heated at 60° for 16 hours. Another 0.48 g (3.7 mmol) of N-benzylcyanamide was added and the mixture was heated at 110° for 20 hours. The mixture was cooled to room temperature, then made basic with aqueous sodium carbonate. The resulting precipitate was collected by filtration, washed with water, and allowed to dry. The solid was stirred in 60 ml of methanol, filtered to remove insolubles, and the filtrate concentrated. The residue was taken up into 40 ml of ethanolic hydrogen chloride, filtered to remove precipitate amounted to 1.5 g (51%) of the pure title compound, mp 174°; nmr (DMSO-d$_6$) ($\delta$): 8.41 (b, 6H); 7.94 (s, 1H); 7.72 (s, 1H); 7.6–7.1 (m, 5H); 4.72 (d, 2H); calcd. for $C_{14}H_{15}N_7S \cdot 2HCl \cdot H_2O$: C, 41.58; H, 4.74; N, 24.25; found: C, 41.97; H, 5.43; N, 23.80.

EXAMPLE 27

2-Guanidino-4-(2-N-phenethylamino-4-imidazoyl)-thiazole dihydrochloride

A mixture of 2.0 g (7.3 mmol) of 2-amino-1-(2-guanidino-4-thiazoyl)ethanone dihydrochloride, 1.61 g (11 mmol) of N-phenethylcyanamide, and 20 ml of water was brought to pH 4.5 by the dropwise addition of 20% sodium hydroxide solution. The mixture was heated at 60° for 16 hours. Another 0.54 g (3.7 mmol) of N-phenethylcyanamide was added and the mixture was heated at 110° for 20 hours. The mixture was cooled to room temperature, then made basic with aqueous sodium carbonate. The resulting precipitate was collected by filtration, washed with water, and allowed to dry. The solid was stirred in 60 ml of methanol, filtered to remove insolubles, and the filtrate concentrated. The residue was taken up into 40 ml of ethanolic hydrogen chloride, filtered to remove insolubles and the filtrate diluted with 200 ml of ether. The resulting precipitate amounted to 0.62 g (20%) of the pure title compound, mp 187°; nmr (DMSO-d$_6$) ($\delta$): 8.48 (b, 6H); 7.94 (s, 1H); 7.70 (s, 1H); 7.38 (s, 5H); 3.72 (m, 2H); 2.96 (t, 3H): calcd. for $C_{15}H_{17}N_7S \cdot 2HCl \cdot H_2O$: C, 43.06; H, 5.06; N, 23.44; found: C, 42.36; H, 5.13; N, 23.30.

EXAMPLE 28

2-Guanidino-4-(2-N-acetamido-4-imidazoyl)thiazole

A mixture of 1.0 g (4.5 mmol) of 2-guanidino-4-(2-amino-4-imidazoyl)thiazole 0.35 (4.5 mmol) of acetyl chloride, and 10 ml of pyridine was stirred at room temperature for 2.5 hours. The supernatant solution was decanted from an insoluble residue and poured into 20 ml of water. This aqueous solution was concentrated and the crude solid residue was triturated with 4 ml of water. The resulting solid was filtered, and dried to give 0.18 g (16%) of the title compound, mp 151°–155°; nmr (DMSO-d$_6$): ($\delta$) 7.38 (s, 1H); 7.2–6.8 (b, 6H); 6.76 (s, 1H); 1.97 (s, 3H). Recrystallization from ethanol/ether afforded analytically pure product; mp 159°–160°; calcd. for $C_9H_{11}N_7OS \cdot H_2O$: C, 38.15; H, 4.62; N, 34.60; found: C, 38.09; H, 4.21; N, 34.88.

EXAMPLE 29

4-Acetylimidazole

A mixture of 6.0 g (54 mmol) of 1-acetylimidazole in 60 ml of tetrahydrofuran was photolyzed in a Rayonet reactor using a quartz vessel at 30° for 16 hours. The mixture was concentrated and the residue chromatographed over 100 g of silica gel using 19:1 chloroform/methanol as eluent. The less polar product was 2-acetylimidazole, mp 133°–135° (0.32 g, 5%). The more polar product amounted to 1.1 g (19%) of 4-acetylimidazole, mp 165°–168°.

EXAMPLE 30

2-Bromo-1-(4-imidazoyl)ethanone hydrobromide

A solution of 0.50 g (4.5 mmol) of 4-acetylimidazole in 10 ml of methanol was stirred a room temperature and 10 drops of 48% hydrogen bromide was added. After stirring at room temperature for 15 minutes, 50 ml of absolute ether was added and the resulting precipitate was collected by filtration and dried to give 0.54 g of the hydrobromide salt, mp 214° (dec). This was dissolved in 10 ml of 48% hydrogen bromide, warmed to 60° and 0.15 ml (3.0 mmol) of bromine was added. After stirring at 60° for 1 hour, the mixture was concentrated and the residue triturated with a mixture of isopropanol/ether. The white crystalline precipitate was filtered, washed with ether, and dried to give 0.42 g (35%) of 2-bromo-1-(4-imidazoyl)ethanone hydrobromide, mp 188°–192°. nmr (DMSO-$d_6$) ($\delta$): 9.02 (s, 1H); 8.45 (s, 1H); 4.84 (s, 2H).

EXAMPLE 31

2-Guanidino-4-(4-imidazoyl)thiazole hydrobromide

A mixture of 0.38 g (1.4 mmol) of 2-bromo-1-(4-imidazoyl)ethanone hydrobromide in 10 ml of acetone was warmed until homogeneous, then 0.17 g (1.4 mmol) of amidinothiourea was added and the mixture was heated at reflux for 0.5 hour. The mixture was cooled and the white precipitate was collected, washed with ether, and dried, thereby affording 0.24 g (60%) of 2-guanidino-4-(4-imidazoyl)thiazole hydrobromide, mp 225° (dec). nmr (DMSO-$d_6$) ($\delta$): 8.20 (s, 1H); 8.0 (b, 4H); 7.77 (s, 1H); 7.36 (s, 1H); high resolution mass spectrum: calcd. $C_7H_8N_6S$: for 208.0531; found: 208.517; calcd. for $C_7H_8N_6S \cdot HBr \cdot H_2O$: C, 27.37; H, 3.60; N, 27.36; found: C, 27.23; H, 3.57; N, 27.64.

EXAMPLE 32

2-Guanidino-4-(4-imidazoyl)thiazole

A mixture of 42 ml of concentrated sulfuric acid and 21 ml of water was cooled to $-10°$ and 1.56 g (22.7 mmol) of sodium nitrate was added. After stirring at $-5°$ for ten minutes, 8.1 ml (78 mmol) of cold 50% hypophosphorous acid was added and stirring was continued for another 10 minutes at $-5°$. A solution of 2.5 g (8.4 mmol) of 2-guanidino-4-(2-amino-4-imidazoyl)-thiazole dihydrochloride in 100 ml of water was added dropwise over 0.5 hour. The reaction was stirred at 50° for 2 hours, then at room temperature for 16 hours. The reaction mixture was diluted with 500 ml of water, made basic with solid sodium carbonate and extracted three times with 150 ml portions of ethyl acetate. The combined ethyl acetate extracts were dried over sodium sulfate, filtered, and evaporating leaving a solid. This solid was taken up into boiling methanol, decolorized with charcoal, and concentrated to a small volume. The resulting solid was collected and dried, thereby affording 90 mg (5%) of 2-guanidino-4-(4-imidazoyl)thiazole identical to the material of Example 31 by thin layer chromatography and high resolution mass spectrometry.

EXAMPLE 33

3-Bromo-4-methoxy-3-buten-2-one 5.0 g (30 mmol) of 3-bromo-4-hydroxy-3-buten-2-one was dissolved in a solution of 100 ml tetrahydrofuran and 10 ml water. To the solution was added 8.7 ml (90 mmol) of dimethylsulfate and 8.3 g (100 mmol) of sodium bicarbonate. The slurry was stirred at 25° for 75 minutes and the solvent was removed in vacuo. The resultant oil and solid were stirred overnight in a mixture of 20 ml diethylether and 150 ml 0.1 N sodium bicarbonate solution. The aqueous layer was separated and extracted with 2×50 ml ether and the combined ether extracts were washed with saturated sodium chloride solution, dried over anhydrous sodium sulfate and concentrated in vacuo to a yellow oil which soon solidified to afford 3.21 g (59%) of 3-bromo-4-methoxy-3-buten-2-one, mp 53°–6°. nmr (DMSO-$d_6$) ($\delta$): 8.22 (s, 1H); 4.03 (s, 3H); 2.37 (s, 3H); Calcd. for $C_5H_7BrO_2$: C, 33.55; H, 3.94; Br, 44.64; found: C, 33.27; H, 3.85; Br, 43.46.

EXAMPLE 34

1-(2-methyl-4-imidazolyl)ethanone 6.3 g (35 mmol) of 3-bromo-4-methoxy-3-buten-2-one, 16.7 g acetamidine hydrochloride (175 mmol) and 29.2 ml triethylamine (210 mmol) were combined in 300 ml tetrahydrofuran and heated at reflux for 6 hours. The solvent was removed in vacuo to a crude orange solid. The crude solid was dissolved in 200 ml ethyl acetate and concentrated to 25 ml by boiling off the solvent. Cooling in ice resulted in crystallization of a yellow solid. This was collected by filtration, washed first with ethyl acetate, then with ether and dried at 25° in vacuo to give 9.995 g (23%) of 1-(2-methyl-4-imidazolyl)ethanone, mp 124°–7°. nmr (DMSO-$d_6$) ($\delta$): 4.61 (s, 1H); 1.41 (s, 3H); 1.39 (s, 3H).

EXAMPLE 35

1-(2-methyl-4-imidazolyl)ethanone 5.75 g (46.3 mmol) of 1-(2-methyl-1-imidazolyl)ethanone was dissolved in 600 ml tetrahydrofuran and photolyzed in a quartz flask with a short wave u.v. light source (2537 nm) for 18 hours. The tetrahydrofuran solution was concentrated in vacuo to an oil and chromatographed on silica gel using 5% methanol in chloroform as eluent to give 2.6 g (45%) 1-(2-methyl-4-imidazolyl)ethanone, mp 123°–5°.

EXAMPLE 36

1-(2-Methyl-4-imidazolyl)-2-bromoethanone hydrobromide 2.40 g (19.3 mmol) of 1-(2-methyl-4-imidazolyl) ethanone was dissolved in 30 ml of 48% hydrogen bromide. To the stirred solution at 25° was added over a 5 minute period 3.36 g (21 mmol) of bromine dissolved in 5 ml 48% hydrogen bromide. The reaction was heated to 70° for 2.5 hours and then concentrated in vacuo to a dark oil. A mixture of isopropyl alcohol/ether was added and trituration of the oil gave a solid. This was collected by filtration and washed with ether to give 2.8 g (51%) of 1-(2-methyl-4-imidazolyl)-2-bromoethanone hydrobromide, mp 181° (dec.); nmr (DMSO-$d_6$) ($\delta$): 8.71 (s, 1H); 4.77 (s, 2H); 2.63 (s, 3H).

EXAMPLE 37

2-Guanidino-4-(2-methyl-4-imidazolyl)thiazole 2.8 g (9.86 mmol) of 1-(2-methyl-4-imidazolyl)-2-bromo ethanone hydrobromide was dissolved in 10 ml water. Saturated sodium bicarbonate solution was added to pH 10 and the resultant solid was collected by filtration and washed with 15 ml water. The dried free base was heated at reflux in 50 ml acetone. To the refluxing clear acetone solution was added 1.2 g (9.86 mmol) of amidinothiourea. Solution occurred immediately and within a minute a solid began to form. After 1 hour reflux the slurry was cooled and the solid was collected by filtration and was washed with acetone followed by ether to give 2.37 g (79%) of 2-guanidino-4-(2-methyl-4-imidazolyl)thiazole hydrobromide, mp 158° (dec.); nmr (DMSO-d$_6$) (δ): 7.71 (s shoulder on broad s, 1H); 7.56 (broad s, 4H); 4.32 (s, 1H); 2.51 (s, 3H); calcd. for C$_8$H$_{10}$N$_6$S.HBr: C, 31.69; H, 3.66; N, 27.72; found: C, 31.46; H, 4.30; N, 27.28.

EXAMPLE 38

1-Acetyl-4-methylimidazole

A mixture of 50 g (609 mmol) of 4-methylimidazole in 250 ml of toluene was stirred at room temperature under nitrogen and 239 g (304 mmol) of acetyl chloride was added. The mixture was stirred at room temperature for 5 hours, filtered to remove insolubles and the filtrate concentrated giving 19 g (50%) of 1-acetyl-4-methyl-imidazole as a yellow oil which crystallizes on standing. nmr (CDCl$_3$) (δ): 8.06 (s, 1H); 7.17 (s,1H); 2.57 (s, 3H); 2.23 (s, 3H).

EXAMPLE 39

5-Acetyl-4-methylimidazole

A solution of 5.0 g (40.3 mmol) of 1-acetyl-4-methylimidazole in 700 ml of dry tetrahydrofuran was photolyzed in a quartz flask with a short wave ultraviolet light source (254 nm) for 24 hours. The tetrahydrofuran solution was concentrated in vacuo to give an oil which was chromatographed on silica gel using 5% methanol in chloroform as eluent to give 1.91 g (38%) of 5-acetyl-4-methylimidazole as a white solid, mp 140°-142°. nmr (CDCl$_3$/D$_6$DMSO) (δ): 7.45 (s, 1H); 2.52 (s, 3H); 2.48 (s, 3H).

EXAMPLE 40

1-(4-Methyl-5-imidazolyl)-2-bromoethanone

A solution of 1.57 g (12.6 mmol) of 5-acetyl-4-methylimidazole in 15 ml of concentrated hydrobromic acid was warmed to 50° and a solution of 2.01 g (12.6 mmol) of bromine in 15 ml of concentrated hydrobromic acid was added over 0.75 hour. The mixture was stirred at 50° for 1.25 hour, then concentrated. The residue was triturated with isopropyl alcohol and the white solid was collected by filtration. This amounted to 2.78 g (78%) of 1-(4-methyl-5-imidazolyl)-2-bromoethanone hydrobromide: nmr (D$_6$DMSO) (δ): 9.40 (s, 1H); 4.87 (s, 2H); 2.65 (s, 3H). This material was converted to its free base by stirring for 15 minutes in 50 ml of saturated sodium bicarbonate solution to give, after collection by filtration and drying, 1-(4-methyl-5-imidazolyl)-2-bromoethanone as a white powder.

EXAMPLE 41

2-Guanidino-4-(4-methyl-5-imidazolyl)thiazole hydrobromide

A mixture of 1.65 g (8.13 mmol) of 1-(4-methyl-5-imidazolyl)-2-bromoethanone in 165 ml of acetone was heated until homogeneous. 0.96 g (8.13 mmol) of amidinothiourea was added and the mixture was heated at reflux for 1 hour. The mixture was allowed to cool to room temperature and the resulting precipitate was collected by filtration. This solid amounted to 0.98 g (40%) of 2-guanidino-4-(4-methyl-5-imidazolyl)thiazole hydrobromide, mp 245° (dc); nmr (D$_6$DMSO) (δ): 8.52 (s, 1H); 7.67 (b, 4H); 7.20 (s, 1H); 2.49 (s, 3H). Anal Calcd. for C$_8$H$_{10}$N$_6$S.HBr: C, 31.69, H, 3.66; N, 27.72; Found: C, 31.80; H, 3.90; N, 26.90.

EXAMPLE 42

1-Acetyl-2,4-dimethylimidazole

A solution of 9.6 g (0.10 M) of 2,4-dimethylimidazole in 50 ml of chloroform and 50 ml of toluene was stirred at room temperature and 3.6 ml (0.05 M) of acetyl chloride was added via syringe over 1 minute. The mixture was stirred at room temperature for 2 hours, then the mixture was filtered to remove insoluble solids, and the filtrate concentrated leaving 6.9 g (100%) of 1-acetyl-2,4-dimethylimidazole as a white crystalline solid: nmr (CDCl$_3$) (δ): 7.00 (s, 1H); 2.68 (s, 3H); 2.57 (s, 3H); 2.21 (s, 3H).

EXAMPLE 43

5-Acetyl-2,4-dimethylimidazole

A solution of 6.9 g (0.05 M) of 1-acetyl-2,4-dimethylimidazole in 700 ml of dry tetrahydrofuran was photolyzed in a quartz flask with a short wave ultraviolet light source (254 nm) for 40 hours. The tetrahydrofuran solution was concentrated in vacuo to give an oil which was chromatographed on silica gel using 5% methanol in chloroform as eluent to give 2.8 g (41%) of 5-acetyl-2,4-dimethylimidazole as a white solid, mp 83°-87°. Recrystallization from isopropyl ether gave analytically pure material, mp 87°-88°. nmr (CDCl$_3$) (δ): 2.53 (s, 6H); 2.40 (s, 3H). Anal. Calcd. for C$_7$H$_{10}$N$_2$O: C, 60.85; H, 7.30; N, 20.27; found: C, 60.66; H, 7.26; N, 20.09.

EXAMPLE 44

1-(2,4-Dimethyl-5-imidazolyl)-2-bromoethanone

A solution of 1.0 g (7.24 mmol) of 5-acetyl-2,4-dimethylimidazole in 15 ml of concentrated hydrobromic acid was warmed to 50° and 1.16 g (7.25 mmol) of bromine was added dropwise over 1 minute. The mixture was then heated at 50°-60° for 1 hour. The mixture was concentrated and the solid residue was triturated with 30 ml of saturated sodium bicarbonate solution. The insoluble material was collected by filtration, washed with water, and dried in vacuo to give 1.12 g (71%) of 1-(2,4-dimethyl-5-imidazolyl)-2-bromoethanone as a white solid, mp 128°-132°. nmr (D$_6$DMSO) (δ): 4.40 (s, 2H); 2.27 (s, 3H); 2.13 (s, 3H).

EXAMPLE 45

2-Guanidino-4-(2,4-dimethyl-4-imidazolyl)thiazole hydrobromide hemihydrate

A solution of 1.0 g (4.6 mmol) of 1-(2,4-dimethyl-5-imidazolyl)-2-bromoethanone in 50 ml of acetone was warmed and 0.55 g (4.6 mmol) of amidinothiourea was added. The mixture was heated at reflux for 1 hour, during which time a white solid precipitated. The precipitate was collected, washed with acetone, and dried to give 1.12 g (77%) of 2-guanidino-4-(2,4-dimethyl-5-imidazolyl)thiazole hydrobromide hemihydrate as a white solid, mp 273° (dc). nmr (D$_6$DMSO) (δ): 8.4–7.2 (b, 7H); 7.00 (s, 1H); 2.50 (s, 3H); 2.38 (s, 3H). Anal. Calcd. for C$_7$H$_{12}$N$_6$S.HBr.½H$_2$O: C, 33.14; H, 4.33; N, 25.76; S, 9.83. Found: C, 33.47; H, 4.19; N, 25.93; S, 9.91.

EXAMPLE 46

2-Guanidino-4-(2-N-phenylamino-4-imidazolyl)thiazole

A mixture of 2.3 g (8.5 mmol) of 2-amino-1-(2-guanidino-4-thiazolyl)ethanone dihydrochloride, 2.0 g (17 mmol) of N-phenylcyanamide and 40 ml of water was heated at 50° for 19 hours. The dark solution was filtered to remove insolubles, and the filtrate was washed with chloroform. The aqueous filtrate was made basic with saturated sodium bicarbonate solution and the resulting precipitate was collected by filtration, washed with water, ether, then acetonitrile to give a brown solid. This was dissolved in ethanolic hydrogen chloride and ether was added resulting in the precipitation of a solid. Recrystallization from n-propanol/acetonitrile gave 479 mg of 2-guanidino-4-(2-N-phenylamino-4-imidazolyl)thiazole dihydrochloride, mp 245°–247° (dc). nmr (D$_6$DMSO) (δ): 8.2–8.0 (b, 4H); 7.76 (s, 1H); 7.4–7.0 (s+b, 5H). High resolution mass spectrum, calcd. for $C_{13}H_{13}N_7S$: 299.0953; found: 299.0964.

EXAMPLE 47

3-Bromo-4-ethoxy-3-buten-2-one

A mixture of 400 ml absolute ethanol and 60 ml toluene was heated to reflux and 20 ml of azeotrope was removed via a Dean Stark trap. To the ethanol-toluene solution was added 33.0 g (0.2 mol) of 3-bromo-4-hydroxy-3-buten-2-one and reflux was continued for 2 hours during which period three aliquots of 20 ml of ethanol-toluene were removed via the trap. The solution was concentrated in vacuo to give 38.6 g (100%) of 3-bromo-4-ethoxy-3-buten-2-one as a mobile oil. nmr (DMSO-6) (δ): 8.21 (s, 1H); 4.23 (q, 2H); 2.33 (s, 3H); 1.31 (s, 3H).

EXAMPLE 48

2-Hydroxymethyl-4-acetylimidazole 9.7 g (0.05 mol) of 3-bromo-4-ethoxy-3-buten-2-one was combined with 5.53 (0.05 mol) of hydroxyacetamidine hydrochloride in 100 ml acetone to form a slurry. To the slurry at 25° was added 11.5 g (0.1 mol) of 1,1,3,3-tetramethylguanidine over a period of 5 minutes. After stirring for 48 hours the slurry was filtered and the mother liquors were concentrated in vacuo to an oil which was chromatographed on silica gel 60 (E. Merck) using chloroform as eluent to give 1.48 g (21%) of 2-hydroxymethyl-4-acetylimidazole, mp 147°–148°. nmr (DMSO-d$_6$) (δ): 7.73 (s, 1H); 5.46 (very broad s, 1H); 4.5 (broad s, 2H); 2.4 (s, 3H).

EXAMPLE 49

2-Hydroxymethyl-4-bromoacetylimidazole hydrobromide 1.826 g (0.013 mol) of 2-hydroxymethyl-4-acetylimidazole was dissolved in 40 ml of 48% hydrobromic acid and 2.1 g (0.013 mol) of bromine was added. The reaction was warmed at 80° for 2 hours and then concentrated in vacuo to a solid. This material was triturated with isopropylether and the resultant solid was collected by filtration and was washed with ether and dried to give 2.2 g (56%) of 2-hydroxymethyl-4-bromoacetylimidazole hydrobromide, mp 183° with decomposition. nmr (DMSO-d$_6$) (δ): 8.8 (s, 1H); 4.8 (s, 2×2H).

EXAMPLE 50

2-Guanidino-4-(2-hydroxymethyl-4-imidazolyl)thiazole hydrobromide 1.78 g (0.0059 mol) of 2-hydroxymethyl-4-bromoacetylimidazole hydrobromide was dissolved in water and saturated sodium bicarbonate solution was added to precipitate the free base. This material was collected by filtration and dried and combined with 956 mg (0.0081 mol) of amidinothiourea in 60 ml acetone and heated to 70°. After 15 minutes heating a solid formed. The reaction mixture was cooled and the resultant solid was collected by filtration to give 1.65 g (87%) 2-guanidino-4-(2-hydroxymethyl-4-imidazolyl)thiazole hydrobromide, mp>310°. A sample was converted to the free base by dissolving in hot water and adding sodium bicarbonate solid to pH 10 to precipitate 2-guanidino-4-(2-hydroxymethyl-4-imidazolyl)thiazole free base. This material was dried over toluene at high vacuum to give a light tan solid, mp 208°–209° with decomposition. nmr (DMSO-d$_6$) (δ): 7.16 (s, 1H); 6.83 (broad s, 4H) 6.68 (s, 1H); 4.45 (s, 2H); 3.46 (very broad s, 1H). High resolution mass spectrum, calcd for $C_8H_{10}N_6OS$: 238.0638; found: 238.0654.

EXAMPLE 51

The gastric acid antisecretory activity of compounds of the present invention was determined in overnight fasted, conscious Heidenhain pouch dogs. Pentagastrin (Pentavlon-Ayerst was used to stimulate acid output by continuous infusion into a superficial leg vein at doses earlier determined to stimulate near maximal acid output from the gastric pouch. Gastric juice was collected at 30 minute intervals following the start of a pentagastrin infusion and measured to the nearest 0.1 ml. Ten collections were taken for each dog during an experiment. Acid concentration was determined by titrating 1.0 ml of gastric juice to pH 7.4 with 0.1 N sodium hydroxide using an Autoburette and a glass electrode pH meter (Radiometer).

Drug or vehicle was given intravenously 90 minutes following the start of the pentagastrin infusion, at a dose of 1 mg/kg. Gastric acid antisecretory effects were calculated by comparing the lowest acid output after drug administration with the mean acid output immediately before drug.

The results obtained showed that the compounds of Examples 4, 5, 6, 7, 11, 13, 15, 17, 20, 21, 22, 23, 24, 25, 26, 27, 28, 31, 37, 41, 45 and 50, all inhibited gastric acid secretion at least 15% at a dose of 1 mg/kg.

EXAMPLE 52

The histamine-H$_2$ antagonist activity of compounds of the present invention was determined by the following procedure:

Guinea pigs are killed rapidly with a blow to the head, the heart removed and the right atria dissected free. Atria are suspended, isometrically, in a temperature-controlled (32°±2°) tissue bath (10 ml containing oxygenated (95% O$_2$; 5% CO$_2$) Krebs-Henseleit buffer (pH 7.4) and are allowed to stabilize approximately one hour during which time the tissue bath is flushed several times. Individual atrial contractions are followed with a force-displacement transducer connected to a cardiotachometer and Grass polygraph recorder. After obtaining a dose-response curve to histamine, the bath containing each atrium is flushed several times with fresh buffer and the atria re-equilibrated to basal rates. Following the return to basal rate, test compounds are added at selected final concentrations and the histamine dose-response curve is again determined in the presence of antagonist. Results are expressed as dose-ratios, the ratio of histamine concentrations required to produce one-half of maximal stimulation in the presence and absence of antagonist, and the apparent dissociation constant of the H₂-receptor antagonist pA₂, is determined. The results obtained showed that the compounds of Examples 4, 5, 6, 7, 11, 13, 15, 17, 20, 21, 22, 23, 24, 25, 26, 27, 28, 31, 37, 41, 45, 46 and 50 have pA₂ values of greater than 5.7.

We claim:

1. A compound of the formula

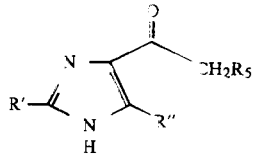

or an acid addition salt thereof, wherein R' is hydrogen, hydroxymethyl, alkyl of 1 to 6 carbon atoms or —(CH₂)ₙAr, wherein n is an integer from 2 to 4; R" is hydrogen or methyl; and Ar is phenyl or phenyl monosubstituted with chloro, bromo, fluoro, alkyl of 1 to 3 carbon atoms or alkoxy of 1 to 3 carbon atoms; and R₅ is halo.

2. A compound of claim 1 wherein R' and R" are each hydrogen and R₅ is chloro or bromo.

3. A compound of claim 1 wherein R' is methyl, R" is hydrogen and R₅ is chloro or bromo.

4. A compound of claim 1 wherein R' is hydrogen, R" is methyl and R₅ is chloro or bromo.

5. A compound of claim 1 wherein R' and R" are each methyl and R₅ is chloro or bromo.

* * * * *